United States Patent
Jewell et al.

(10) Patent No.: US 11,246,327 B2
(45) Date of Patent: Feb. 15, 2022

(54) PALATABILITY ENHANCERS FOR FOODS DESIGNED FOR DOGS AND CATS WITH RENAL INSUFFICIENCY

(71) Applicant: Hill's Pet Nutrition, Inc., Topeka, KS (US)

(72) Inventors: Dennis Jewell, Lawrence, KS (US); Melissa Vanchina, Lawrence, KS (US); Jodi Vondran, Wamego, KS (US)

(73) Assignee: Hills Pet Nutrition, Inc., Topeka, KS (US)

( * ) Notice: Subject to any disclaimer, the term of this patent is extended or adjusted under 35 U.S.C. 154(b) by 0 days.

(21) Appl. No.: 16/550,678

(22) Filed: Aug. 26, 2019

(65) Prior Publication Data

US 2019/0373916 A1 Dec. 12, 2019

Related U.S. Application Data

(62) Division of application No. 15/034,669, filed as application No. PCT/US2013/068378 on Nov. 5, 2013, now abandoned.

(51) Int. Cl.

| | |
|---|---|
| A23K 20/147 | (2016.01) |
| A23K 20/26 | (2016.01) |
| A23K 50/48 | (2016.01) |
| A23K 50/40 | (2016.01) |
| A23K 20/158 | (2016.01) |
| A23K 20/22 | (2016.01) |
| A23K 20/24 | (2016.01) |
| A23K 20/10 | (2016.01) |

(52) U.S. Cl.
CPC ............ *A23K 20/147* (2016.05); *A23K 20/10* (2016.05); *A23K 20/158* (2016.05); *A23K 20/22* (2016.05); *A23K 20/24* (2016.05); *A23K 20/26* (2016.05); *A23K 50/40* (2016.05); *A23K 50/48* (2016.05)

(58) Field of Classification Search
CPC .... A23K 20/10; A23K 20/147; A23K 20/158; A23K 20/22; A23K 20/24; A23K 20/26
See application file for complete search history.

(56) References Cited

U.S. PATENT DOCUMENTS

| | | |
|---|---|---|
| 6,254,920 B1 | 7/2001 | Brunner |
| 7,244,460 B2 | 7/2007 | Lee et al. |
| 7,744,917 B2 | 6/2010 | Gross et al. |
| 7,867,540 B2 | 1/2011 | Didzbalis et al. |
| 8,226,973 B2 | 7/2012 | Pan |
| 8,647,660 B2 | 2/2014 | Jewell |
| 9,149,062 B2 | 10/2015 | Friesen et al. |
| 9,173,427 B2 | 11/2015 | Friesen et al. |
| 9,255,296 B2 | 2/2016 | Al-Murrani et al. |
| 2003/0086961 A1 | 5/2003 | Yu et al. |
| 2005/0037108 A1 | 2/2005 | Lin et al. |
| 2008/0233244 A1* | 9/2008 | Swenson ................ A23K 50/42 426/72 |
| 2008/0293621 A1 | 11/2008 | Allen et al. |
| 2009/0275505 A1 | 11/2009 | Wedekind |
| 2011/0171318 A1* | 7/2011 | Friesen ................... A61P 13/12 424/601 |
| 2013/0122147 A1 | 5/2013 | Tissot-Favre et al. |
| 2013/0287930 A1 | 10/2013 | Bramoulle et al. |
| 2014/0227386 A1 | 8/2014 | Niceron et al. |
| 2014/0272028 A1* | 9/2014 | Donavon ............... G06Q 50/04 426/231 |

FOREIGN PATENT DOCUMENTS

| | | |
|---|---|---|
| CN | 1251021 | 4/2000 |
| CN | 1253738 | 5/2000 |
| EP | 3482639 A1 | 5/2019 |
| JP | 2008-522614 | 7/2008 |
| JP | 2008-301824 | 12/2008 |
| WO | 1992/003931 | 3/1992 |
| WO | 2000/030456 | 6/2000 |
| WO | 2006/108249 | 10/2006 |
| WO | 2006/119049 | 11/2006 |
| WO | 2012/115648 | 8/2012 |
| WO | 2012/148769 | 11/2012 |
| WO | 2013/094575 | 6/2013 |
| WO | 2015/066009 | 5/2015 |
| WO | 2015/069212 A1 | 5/2015 |

OTHER PUBLICATIONS

K4P2O7 molecular weight; accessed on Mar. 2, 2021; available at: https://www.convertunits.com/molarmass/K4P2O7 (Year: 2021).*
Nutrient Requirement of Cats, National Academy Press, Wash DC published 1986, pp. 15-17 (Year: 1986).
Nutrient Requirement of Dogs, National Academy Press, Wash DC published 1985, pp. 7-8 (Year: 1985).
Anonymous, Third Party Observation in International Application No. PCT/US2013/068378, submitted Feb. 22, 2016.
Boyce, et al., "Effects of ageing on smell and taste", Postgrad Medical Journal, 2006, vol. 82, p. 239-241.
Elliot et al., "Survival of cats with naturally occurring chronic renal failure: effect of dietary management", Journal of Small Animal Practice, 2000, vol. 41, No. 6, p. 235-242.
Finco et al., 1992, "Effects of dietary phosphorus and protein in dogs with chronic renal failure," American J. Veterinary Research 53(12):2264-2271.
Gutierrez et al., "Sodium- and Phosphorus-Based Food Additives: Persistent but Surmountable Hurdles in the Management of Nutrition in Chronic Kidney Disease", Advances in Chronic Kidney Disease, 2013, vol. 20, Issue 2, p. 150-156.
Hill's Evidence-Based Clinical Nutrition for Dermatology Specialists, 2007, accessed Apr. 18, 2016, (http://web.archive.org/web/20150914194228/http://www.hillsvet.com/conference-documents/dermatology/P9208__EBCN__Derm__Specialists.pdf), p. 1-42.
International Search Report and Written Opinion in International Application No. PCT/US2013/068378, dated Jul. 28, 2014.

(Continued)

*Primary Examiner* — Walter A Moore

(57) ABSTRACT

The present invention relates to compositions that enhances the palatability of pet foods designed for companion animals, e.g. dogs and cats, with renal insufficiency, and for methods of their manufacture.

10 Claims, No Drawings

(56) References Cited

OTHER PUBLICATIONS

Molecular Weight of K4P2O7, accessed Apr. 18, 2016, (http://www.convertunits.com/molamnass/K4P2O7), 2 pages.

Ross et al., "Clinical evaluation of dietary modification for treatment of spontaneous chronic kidney disease in cats", Journal of the American Veterinary Medical Association, 2006, vol. 229, No. 6, p. 949-957.

Schiffman, 1997, "Taste and smell losses in normal aging and disease," The Journal of the American Medical Association 278(16):1357-1362.

Brown et al., "Interventional Nutrition for Renal Disease," Clinical Techniques in Small Animal Practice, vol. 13, No. 4 Nov. 1998, pp. 217-223.

Molecular weight of Na4P2O7, accessed Oct. 11, 2020, (http://www.convertunits.com/molarmass/Na4P2O7), 2 pages.

Parker et al., "Nutritional Management of Protein-Losing Nephropathy in Dogs," Vetlearn.com, Jul. 2012, Compendium: Continuing Education for Veterinarians, pp. E1-E5.

\* cited by examiner

PALATABILITY ENHANCERS FOR FOODS DESIGNED FOR DOGS AND CATS WITH RENAL INSUFFICIENCY

FIELD

The present invention relates to compositions that enhance the palatability of pet foods designed for companion animals with renal insufficiency, e.g. dogs and cats, and for methods of their manufacture.

BACKGROUND

It is known that cats with renal disease benefit from consuming foods that are restricted in phosphorus. See, e.g., "Survival of cats with naturally occurring chronic renal failure: effect of dietary management," J. Elliott et al.; Journal of Small Animal Practice Volume 41, Issue 6, pages 235-242, June 2000. It is also known that dietary protein and phosphorus restriction enhances quality and length of life in cats with renal failure. See "Clinical evaluation of dietary modification for treatment of spontaneous chronic kidney disease in cats," Sheri J. Ross, et al., Journal of the American Veterinary Medical Association Sep. 15, 2006, Vol. 229, No. 6, Pages 949-957. Because a universal constant of renal disease is inappetence, there is a significant need for foods which are tasty and preferred by animals, for example cats and dogs, with renal disease. Thus there is a need for compositions and methods that enhance the palatability of pet foods for companion animals suffering from renal disease and insufficiency. This invention is directed to these, as well as, other, important ends.

SUMMARY

Unless otherwise indicated, the terms "%" or "percent" when used in connection with an ingredient of the compositions of the invention is intended to refer to the percent by weight of the indicated ingredient in the composition.

In one aspect, the invention provides palatability enhancing compositions for use in pet foods, where the palatability enhancing compositions include protein and phosphorus in a ratio of more than 17:1; or more than 15:1; or more than 12:1; or 11:1, 10:1, 9:1, 8:1, 7:1 6:1 or 5:1.

In some embodiments, the invention provides pet foods containing a palatability enhancing composition as described above. In some embodiments, the pet food compositions are designed for animals, e.g. companion animals, e.g. dogs and cats, suffering from renal insufficiency or disease.

In some embodiments, the palatability enhancing composition is present in the pet food composition in an amount of up to 10% by weight, or up to 5% by weight, or from 1% to 5% by weight, or from 1% to 4% by weight, or 1%, 2%, 3%, 4% or 5% by weight of the pet food composition.

The present invention also provides methods for enhancing the palatability of the pet food composition, comprising the step of treating the pet food composition to include a palatability enhancing composition of the invention.

The present invention also provides methods for treating a companion animal; and/or ameliorating a symptom in a companion animal; and/or increasing food consumption of a companion animal that is suffering from a renal deficiency, comprising the step of feeding the companion animal a pet food composition that comprises a palatability enhancing composition of the invention as described above.

DETAILED DESCRIPTION

It has been discovered in accordance with the present invention that manipulation of the protein to phosphorus ratio of palatability enhancing compositions can result in a specific palatability enhancement effect on animals with renal deficiency. Specifically, maintaining a protein to phosphorus ratio of more than 17:1; or more than 15:1; or more than 12:1; or 11:1, 10:1, 9:1, 8:1, 7:1 6:1 or 5:1 results in increased palatability specifically in animals with renal deficiency, e.g., cats and dogs, while not showing the same effect on healthy animals. Thus, the compositions described herein are especially beneficial for animals with renal deficiency, which tend to suffer from loss of appetite. While the palatability enhancer having a relatively high phosphorous level enhances consumption, the total phosphorous level can be kept a low level, as is desirable for these animals.

Accordingly, the present invention provides palatability enhancing compositions for use in pet foods, where the palatability enhancing compositions include protein and phosphorus in a ratio of more than 17:1; or more than 15:1; or more than 12:1; or 11:1, 10:1, 9:1, 8:1, 7:1, 6:1 or 5:1; and for example at least 3:1, e.g., at least 5:1.

Typically, palatability enhancers are formulated to ensure that the whole food composition meets the nutritional needs of the target animal. By maintaining a specific range for the ratio of protein to phosphorus in the palatability enhancers in accordance with the present invention, the palatability enhancer more precisely fits with the nutrient needs of the animal.

In some embodiments, the invention provides pet foods that contain a palatability enhancing composition as described above. In some embodiments, the pet food composition is one that is designed for animals with renal insufficiency or disease.

Generally, the palatability enhancing composition is present in the pet food composition in an amount effective to enhance palatability. In some embodiments, the palatability enhancing composition is present in the pet food composition in an amount of up to 10% by weight, or up to 5% by weight, or from 1% to 5% by weight, or from 1% to 4% by weight, or 1%, 2%, 3%, 4% or 5% by weight of the pet food composition.

The palatability enhancing compositions of the invention can be added to the pet food composition by a variety of means known in the art, including for example by coating the pet food (e.g., a pet food kibble) with a palatability enhancing composition of the invention. For example, in one embodiment, the palatability enhancer is applied to particles or pieces of extruded, dry or semi-dry cat food. Alternatively, the palatability enhancing composition of the invention can be incorporated into the pet food (or example an extruded pet food) during production. Accordingly, the present invention also provides methods for enhancing the palatability of the pet food composition, comprising the step of treating the pet food composition to include a palatability enhancing composition of the invention. As used herein, "treating the pet food composition" is intended to include any manner of adding or incorporating the palatability enhancing compositions of the invention into or on the surface of the pet food composition.

The present invention also provides methods for treating a companion animal; and/or ameliorating a symptom in a companion animal; and/or increasing food consumption of a companion animal; where the companion animal is suffering from a renal deficiency, comprising the step of feeding the companion animal a pet food composition that comprises a palatability enhancing composition of the invention as described above.

The palatability enhancers of the invention can be used with a wide variety of pet foods to increase palatability. Such compositions are not intended to be limited to a specific listing of ingredients because such ingredients will depend on such factors as, for example, the desired nutritional balance for the specific type of pet, and availability of ingredients to the manufacturer. In addition to the proteinaceous and farinaceous materials, the pet food composition generally may include vitamins, minerals, and other additives such as flavorings, preservatives, emulsifiers and humectants. The nutritional balance, including the relative proportions of vitamins, minerals, fat, protein and carbohydrate, is determined according to dietary standards known in the veterinary art. For example, the nutritional balance of a cat food composition is determined according to the known dietary requirements for cats.

Preferably, the pet food is one that is designed for animals with renal insufficiency or disease. Such foods are known in the art to have restricted amounts of protein and phosphorus relative to foods designed for healthy animals. For example, pet food compositions designed for animals with renal insufficiency or disease may typically contain approximately 25%-30% protein, whereas foods for healthy animals typically contain 30%-50% protein. Therefore, the amount of palatability enhancer added to the food preferably does not increase amounts of protein and phosphorus to levels above those levels suitable for animals with renal insufficiency or disease.

The palatability enhancers of the invention improve the palatability of wet, dry and semi-dry pet foods, and are particularly suitable for dry and semi-dry cat foods.

The invention thus provides, in one embodiment, a palatability enhancer (Enhancer 1) comprising a protein to phosphorus ratio of more than 17:1; or more than 15:1; or more than 12:1; or 11:1, 10:1, 9:1, 8:1, 7:1, 6:1 or 5:1, and for example at least 3:1 or at least 5:1. For example,
  1.1. Enhancer 1 wherein the protein to phosphorous ratio is between 5:1 and 15:1, e.g., from 10:1 to 12:1.
  1.2. Enhancer 1 comprising:
    from 38% to 47% protein;
    from 5% to 8% fat;
    up to 0.5% crude fiber;
    from 15% to 27% ash; and
    from 4% to 6% phosphorus.

The invention further provides a pet food composition (Composition 1) comprising a palatability enhancing amount of a palatability enhancer selected from Enhancer 1, et seq. for example:
  1.1. Composition 1 wherein the composition is designed for animals, for example companion animals, suffering from renal insufficiency or disease.
  1.2. Composition 1 or 1.1 wherein the composition is palatable and nutritionally complete for a cat or a dog.
  1.3. Any foregoing composition which is a wet, dry or semi-dry food.
  1.4. Any foregoing composition wherein the palatability enhancer has been applied to the surface of a dry or semi-dry food.
  1.5. Any foregoing composition wherein the palatability enhancer is present in an amount effective to enhance palatability, for example up to 10% by weight, or up to 5% by weight, or from 1% to 10, e.g., % 1% to 5% by weight, or from 1% to 4% by weight, or 1%, 2%, 3%, 4% or 5% by weight of the pet food composition.
  1.6. Any foregoing composition wherein the pet food composition is designed for cats with renal insufficiency or disease.
  1.7. Any foregoing composition wherein the pet food composition is designed for dogs with renal insufficiency or disease.
  1.8. Any foregoing composition where the palatability enhancer comprises:
    from 38% to 47% protein;
    from 5% to 8% fat;
    up to 0.5% crude fiber;
    from 15% to 27% ash; and
    from 4% to 6% phosphorus.
  1.9. Any foregoing composition, which is palatable and nutritionally complete for a cat.
  1.10. Any foregoing composition, which is feline diet comprising, on a dry matter basis:
    Protein 25-35%
    Fat 15-30%
    Crude Fiber 1-10%
    Calcium 0.45-1.0%
    Phosphorus 0.35-0.70%
    Sodium 0.2-1.0%
    Potassium 0.5-1.0%
  1.11. Any foregoing composition, which is a feline diet comprising the following components, in approximately (e.g., ±5%) the following amounts by weight on a dry matter basis:
    Protein 27.9%
    Fat 20.3%
    Crude Fiber 1.9%
    Calcium 0.70%
    Phosphorus 0.49%
    Sodium 0.24%
    Potassium 0.76%

The invention provides in another embodiment a method for enhancing the palatability of a pet food composition, comprising the step of treating the pet food composition to include a palatability enhancing amount of any of Enhancer 1, et seq., e.g., to provide any Composition 1, et seq.

The invention provides in another embodiment a method for treating a companion animal that is suffering from a renal deficiency or disease, comprising the step of feeding the companion animal any of Composition 1, et seq.

The invention provides in another embodiment a method for ameliorating a symptom in a companion animal that is suffering from a renal deficiency or disease, comprising the step of feeding the companion animal any of Composition 1, et seq.

The invention provides in another embodiment a method for increasing food consumption of a companion animal that is suffering from a renal deficiency or disease, comprising the step of feeding the companion animal any of Composition 1, et seq., or adding to the animals food a palatability enhancing amount of any of Enhancer 1, et seq.

The following examples are further illustrative of the nature of the present invention, but it is understood that the invention is not limited thereto. All amounts and proportions referred to herein and in the appended claims are by weight, unless otherwise indicated.

Example 1—Preparation and Testing of Pet Food Palatability Enhancer

A standard cat food palatability enhancer (Standard) having a phosphorus to protein ratio of 24.7 is compared to a palatability enhancer in accordance with the present invention (Test) having a phosphorus to protein ratio of 11.4. The palatability enhancers had the following compositions:

| Enhancer Nutrient | Test g/100 g | Standard g/100 g |
|---|---|---|
| Moisture | 7.49 | 3.00 |
| Protein | 42.08 | 34.00 |
| Fat | 6.67 | 7.11 |
| Crude Fiber | 0.20 | 0.54 |
| Ash | 21.52 | 39.93 |
| Phosphorus | 4.79 | 8.40 |
| Protein to Phosphorus (%) | 8.78 | 4.05 |

The palatability enhancers are used in the same food at levels which provided equal palatability in normal cats. There are also no significant differences in the nutrient content of the two foods, with the food with the standard palatability enhancer containing 28.0% protein and 0.48% phosphorus while the food with the palatability enhancer according to the present invention contained 28.0% protein and 0.51% phosphorus (nutrient concentrations on a dry matter basis).

Intake ratios are considered measurements of palatability and food preference. Intake ratio is calculated by the following equation: (Test Food Consumed)/(Test Food Consumed+Standard Food Consumed). Thus, an intake ratio of 0.50 indicates that there is no preference between the two foods, while ratios which are statistically greater than 0.5 show that there is a significant preference for the test food. When the palatants are fed to normal healthy animals there is equal palatability in the two foods as shown by an intake ratio of 0.46 (test food/(test+standard)) with the standard food having a slightly higher intake ratio and with 46% of the cats preferring the food with the test palatant. When cats with renal insufficiency are given the same foods the intake ratio is significantly higher than 0.5—specifically at 0.68, with 75% of the cats preferring the food with the test palatant.

The results show that the composition of the invention is specifically preferred by cats with renal insufficiency, and not preferred by normal cats.

While the present invention has been described with reference to embodiments, it will be understood by those skilled in the art that various modifications and variations may be made therein without departing from the scope of the present invention as defined by the appended claims.

The invention claimed is:

1. A method for increasing food consumption of a companion animal that is suffering from a renal deficiency or disease, comprising feeding only the companion animal in need thereof a pet food composition comprising a palatability enhancing amount of a palatability enhancing composition,
   wherein the palatability enhancing composition comprises, on a dry matter basis:
   a protein to phosphorus ratio of from 7:1 to 9:1;
   from 38% to 47% protein;
   from 5% to 8% fat;
   up to 0.5% crude fiber;
   from 15% to 27% ash; and
   from 4% to 6% phosphorus;
   wherein the pet food composition comprises, on a dry matter basis:
   25% to 35% protein;
   15% to 30% fat;
   1% to 10% crude fiber;
   0.45% to 1.0% calcium;
   0.35% to 0.70% phosphorus;
   0.2% to 1.0% sodium; and
   0.5% to 1.0% potassium;
   wherein the palatability enhancing composition is a coating of the pet food composition,
   wherein the palatability enhancing composition is present on the pet food composition in an amount of from 1% to 10% on a dry matter basis, and
   wherein the palatability enhancing composition significantly increases an intake ratio of the pet food composition fed to the companion animal suffering from the renal deficiency or disease relative to an intake ratio of the pet food composition fed to a healthy cat.

2. The method of claim 1, wherein the protein to phosphorus ratio is more than 8:1.

3. The method of claim 1, wherein the pet food composition is a wet cat food composition.

4. The method of claim 1, wherein the companion animal is a cat.

5. The method of claim 1, wherein the palatability enhancing composition does not increase an intake ratio of the pet food composition in the healthy cat.

6. The method of claim 1, wherein the palatability enhancing composition comprises:
   7.49% moisture, on a wet basis;
   42.08% protein, on a dry matter basis;
   6.67% fat, on a dry matter basis;
   0.2% crude fiber, on a dry matter basis;
   21.52% ash, on a dry matter basis;
   4.79% phosphorus, on a dry matter basis; and
   a protein to phosphorus ratio of 8.78.

7. A method for treating a companion animal that is suffering from a renal deficiency or disease, comprising:
   feeding only the companion animal in need thereof a pet food composition comprising a palatability enhancing amount of a palatability enhancing composition,
   wherein the palatability enhancing composition comprises, on a dry matter basis:
   a protein to phosphorus ratio of from 7:1 to 9:1;
   from 38% to 47% protein;
   from 5% to 8% fat;
   up to 0.5% crude fiber;
   from 15% to 27% ash; and
   from 4% to 6% phosphorus;
   wherein the pet food composition comprises, on a dry matter basis:
   25% to 35% protein;
   15% to 30% fat;
   1% to 10% crude fiber;
   0.45% to 1.0% calcium;
   0.35% to 0.70% phosphorus;
   0.2% to 1.0% sodium; and
   0.5% to 1.0% potassium;
   wherein the palatability enhancing composition is a coating of the pet food composition,
   wherein the palatability enhancing composition is present on the pet food composition in an amount of from 1% to 10% on a dry matter basis, and
   wherein the palatability enhancing composition significantly increases an intake ratio of the pet food composition fed to the companion animal suffering from the renal deficiency or disease relative to an intake ratio of the pet food composition fed to a healthy cat; and
   increasing a food intake of the companion animal in need thereof.

8. The method of claim 7, wherein the pet food composition is a wet cat food composition.

9. The method of claim 7, wherein the companion animal is a cat.

10. A method for ameliorating a symptom in a companion animal that is suffering from a renal deficiency or disease, comprising feeding only the companion animal in need thereof a pet food composition comprising a palatability enhancing amount of a palatability enhancing composition, wherein the palatability enhancing composition is a coating of the pet food composition and comprises a protein to phosphorus ratio of 7 to 8.78, and wherein the symptom in the companion animal is inappetence, and wherein the palatability enhancing composition increases an intake ratio of the pet food composition fed to the companion animal suffering from the renal deficiency or disease relative to an intake ratio of the pet food composition fed to a healthy cat.

* * * * *